United States Patent
Mansfield

(10) Patent No.: US 8,177,766 B2
(45) Date of Patent: May 15, 2012

(54) STRETCH LAMINATE, METHOD OF MAKING, AND ABSORBENT ARTICLE

(75) Inventor: Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 871 days.

(21) Appl. No.: 11/811,130

(22) Filed: Jun. 8, 2007

(65) Prior Publication Data

US 2007/0293111 A1    Dec. 20, 2007

Related U.S. Application Data

(60) Provisional application No. 60/812,207, filed on Jun. 9, 2006.

(51) Int. Cl.
| | |
|---|---|
| A61F 13/15 | (2006.01) |
| A61F 13/20 | (2006.01) |
| B29C 65/00 | (2006.01) |
| B65H 81/00 | (2006.01) |

(52) U.S. Cl. ............ 604/385.22; 442/381; 156/196
(58) Field of Classification Search ............ 604/385.22; 428/131, 136, 152; 442/327, 381, 394, 401
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 3,929,135 A | 12/1975 | Thompson | |
| 4,116,892 A | 9/1978 | Schwarz | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,573,986 A | 3/1986 | Minetola et al. | |
| 4,609,518 A | 9/1986 | Curro et al. | |
| 4,610,678 A | 9/1986 | Weisman et al. | |
| 4,629,643 A | 12/1986 | Curro et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,699,622 A | 10/1987 | Toussant et al. | |
| 4,710,189 A | 12/1987 | Lash | |
| 4,785,996 A | 11/1988 | Ziecker et al. | |
| 4,795,454 A | 1/1989 | Dragoo | |
| 4,808,178 A | 2/1989 | Aziz et al. | |

(Continued)

FOREIGN PATENT DOCUMENTS

WO    WO-94/14395 A1    7/1994

(Continued)

*Primary Examiner* — Melanie Hand
(74) *Attorney, Agent, or Firm* — Andrew A Paul; John P. Colbert

(57) ABSTRACT

A stretch laminate includes a first layer including an elastomer film, the first layer having a surface, and a second layer including a nonwoven material, the second layer having a basis weight of less than about 25 gsm and a surface that is attached to the surface of the first layer. The elastomer film has a strength of an engineering tensile strength, at an engineering strain rate of about 600/s, of at least one of about greater than about 14 MPa for a plain specimen or about greater than about 7 MPa for a notched specimen. A method of making the stretch laminate and an absorbent article having at least one region defined by the stretch laminate are also provided.

21 Claims, 5 Drawing Sheets

U.S. PATENT DOCUMENTS

| | | | |
|---|---|---|---|
| 4,834,735 A | 5/1989 | Alemany et al. | |
| 4,834,741 A | 5/1989 | Sabee | |
| 4,842,666 A | 6/1989 | Werenicz | |
| 4,846,815 A | 7/1989 | Scripps | |
| 4,888,231 A | 12/1989 | Angstadt | |
| 4,892,536 A | 1/1990 | Desmarais et al. | |
| 4,894,060 A | 1/1990 | Nestegard | |
| 4,909,803 A | 3/1990 | Aziz et al. | |
| 4,940,464 A | 7/1990 | Van Gompel et al. | |
| 4,946,527 A | 8/1990 | Battrell | |
| 4,968,312 A | 11/1990 | Khan | |
| 4,990,147 A | 2/1991 | Freeland | |
| 5,006,394 A | 4/1991 | Baird | |
| 5,037,416 A | 8/1991 | Allen et al. | |
| 5,062,840 A | 11/1991 | Holt et al. | |
| 5,092,861 A | 3/1992 | Nomura et al. | |
| 5,137,537 A | 8/1992 | Herron et al. | |
| 5,143,679 A | 9/1992 | Weber et al. | |
| 5,147,345 A | 9/1992 | Young et al. | |
| 5,151,092 A | 9/1992 | Buell et al. | |
| 4,842,666 A | 10/1992 | Werenicz | |
| 5,156,793 A | 10/1992 | Buell et al. | |
| 5,167,897 A | 12/1992 | Weber et al. | |
| 5,171,236 A | 12/1992 | Dreier et al. | |
| 5,221,274 A | 6/1993 | Buell et al. | |
| 5,246,433 A | 9/1993 | Hasse et al. | |
| 5,260,345 A | 11/1993 | Desmarais et al. | |
| 5,269,755 A | 12/1993 | Bodicky | |
| 5,269,775 A | 12/1993 | Freeland et al. | |
| 5,306,266 A | 4/1994 | Freeland | |
| 5,342,338 A | 8/1994 | Roe | |
| 5,387,207 A | 2/1995 | Dyer et al. | |
| 5,397,318 A | 3/1995 | Dreier | |
| 5,422,172 A | 6/1995 | Wu | |
| 5,514,121 A | 5/1996 | Roe et al. | |
| 5,518,801 A | 5/1996 | Chappell et al. | |
| 5,540,671 A | 7/1996 | Dreier | |
| 5,554,142 A | 9/1996 | Dreier et al. | |
| 5,554,145 A | 9/1996 | Roe et al. | |
| 5,569,234 A | 10/1996 | Buell et al. | |
| 5,580,411 A | 12/1996 | Nease et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| 5,643,588 A | 7/1997 | Roe et al. | |
| 5,653,703 A | 8/1997 | Roe et al. | |
| 5,714,027 A * | 2/1998 | Taub | 156/204 |
| 5,897,545 A | 4/1999 | Kline et al. | |
| 5,941,864 A | 8/1999 | Roe | |
| 5,957,908 A | 9/1999 | Kline et al. | |
| 5,968,025 A | 10/1999 | Roe et al. | |
| 5,997,520 A | 12/1999 | Ahr et al. | |
| 6,004,306 A | 12/1999 | Robles et al. | |
| 6,013,063 A | 1/2000 | Roe et al. | |
| 6,120,487 A | 9/2000 | Ashton | |
| 6,120,489 A | 9/2000 | Johnson et al. | |
| 6,168,584 B1 | 1/2001 | Allen et al. | |
| 4,795,454 C1 | 6/2001 | Dragoo | |
| 6,428,526 B1 | 8/2002 | Heindel et al. | |
| 6,432,098 B1 | 8/2002 | Kline et al. | |
| 6,475,600 B1 * | 11/2002 | Morman et al. | 428/152 |
| 6,680,422 B2 | 1/2004 | Roe | |
| 6,716,441 B1 | 4/2004 | Osborne et al. | |
| 6,843,134 B2 | 1/2005 | Anderson et al. | |
| 6,915,700 B2 | 7/2005 | Anderson et al. | |
| 2003/0060794 A1 | 3/2003 | Olson | |
| 2003/0124306 A1 | 7/2003 | Morman | |
| 2004/0177709 A1 | 9/2004 | Anderson et al. | |
| 2005/0158513 A1 * | 7/2005 | Peacock et al. | 428/136 |
| 2005/0222546 A1 | 10/2005 | Vargo et al. | |

FOREIGN PATENT DOCUMENTS

| | | |
|---|---|---|
| WO | WO-95/24173 A2 | 9/1995 |
| WO | WO-95/24173 A3 | 10/1995 |
| WO | WO 00/45764 A | 8/2000 |
| WO | WO 00/46023 A2 | 8/2000 |

* cited by examiner

STRETCH LAMINATE, METHOD OF MAKING, AND ABSORBENT ARTICLE

CROSS REFERENCE TO RELATED APPLICATION

This application claims the benefit of U.S. Provisional Application No. 60/812,207, filed Jun. 9, 2006, the substance of which is incorporated herein by reference.

FIELD OF THE INVENTION

The present disclosure generally relates to a stretch laminate and a method of making the same, and to an absorbent article, such as a diaper, a pant, or the like, made using the stretch laminate.

BACKGROUND OF THE INVENTION

Disposable absorbent articles, such as diapers, are designed to contain bodily exudates, such as urine, to prevent the soiling of the wearer's clothing and/or other items (for example, a bed, a chair, a blanket, etc.). The fit of the article to the wearer's body is important in ensuring that these wastes are contained, instead of leaking out. The fit of the article to the wearer's body may be affected by the size of the diaper waist opening, the size of the openings around the thighs, and the length or "pitch" of the diaper.

Disposable absorbent articles are also designed to be cost-effective. That is, the average consumer may have second thoughts about using a product that holds itself out as disposable if the cost per article is too high. Thus, manufacturers generally make such articles for use by individuals with a wide range of body types that may be classified by a broad criterion, such as weight, for example.

It will be recognized that the need to make products that conform to a wide range of body types competes with the desire for the article to fit snugly to the user to contain wastes and limit leakage.

One way in which manufacturers attempt to balance the competing interests of proper fit and variation in body type is through the use of expandable materials. One such group of materials is known as stretch laminates. As the name suggests, these materials are actually composites of individual components that are laminated together, through the use of an adhesive, for example. A typical stretch laminate will attempt to combine an inner layer defined by a material having good elastomeric properties, to accommodate varying body types, with outer layer or layers defined by a fabric-like material, to accommodate user expectations for look and feel.

A complication arises in that the outer layer or layers of these stretch laminates may inhibit the operation of the inner layer having good elasticity. Consequently, stretch laminates often undergo a processing step, known as activation, prior to use in the manufacture of an absorbent article, such as a diaper or pant, for example. During activation, a mechanical deformation is imposed on the laminate so that the composite material will exhibit better elasticity, while providing the desired look and feel.

Unfortunately, the activation process may have unintended consequences for the materials that comprise the laminate. For example, mechanical damage to the inner, elastomer layer, as manifest by ruptures or holes in the elastomer, may occur during the activation process. These holes may be macroscopic, and may be on the order of several millimeters in size. If an excessive number of holes develop, the laminate material may be perceived by the user as defective, or may not provide the desired stretch properties or performance.

One solution has been to use larger thicknesses, or gauges, of material for the inner layer. Another alternative has been to use specialty nonwoven products, designed and manufactured to be compatible with the activation (or ring-rolling) process, for the outer layers. Both of these solutions increase the cost of the resultant laminate.

Thus, it would be desirable to provide new stretch laminates and methods for making stretch laminates. In particular, it would be desirable to provide less expensive laminates produced using less expensive materials.

SUMMARY OF THE INVENTION

In one aspect, a stretch laminate comprises a first layer comprising an elastomer film, the first layer having a surface, and a second layer comprising a nonwoven material, the second layer having a basis weight of less than about 25 gsm and a surface that is attached to the surface of the first layer. The elastomer film having an engineering tensile strength, at an engineering strain rate of about 600/s, of at least one of about greater than about 14 MPa for a plain specimen or about greater than about 7 MPa for a notched specimen.

In another aspect, a method of making a stretch laminate is provided, the method comprising providing an elastomer film, the elastomer film having an engineering tensile strength, at an engineering strain rate of about 600/s, of at least one of about greater than about 14 MPa for a plain specimen or about greater than about 7 MPa for a notched specimen, attaching a nonwoven layer having a basis weight of less than about 25 gsm to the elastomer film to form an assembly, and activating the assembly of the elastomer film and the nonwoven layer.

In a further aspect, an absorbent article having a waist region and a crotch region is provided, the article comprising a backsheet having a longitudinal axis, a topsheet attached to the backsheet and having a body-facing surface, an absorbent core disposed between the backsheet and the topsheet, and a stretch laminate defining at least one region of the absorbent article. The stretch laminate comprises a first layer comprising an elastomer film, the first layer having a surface, and a second layer comprising a nonwoven material, the second layer having a basis weight of less than about 25 gsm and a surface that is attached to the surface of the first layer. The elastomer film having a strength of an engineering tensile strength, at an engineering strain rate of about 600/s, of at least one of about greater than about 14 MPa for a plain specimen or about greater than about 7 MPa for a notched specimen.

Additional aspects of the disclosure are defined by the claims of this patent.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Definitions

Figure 1A:
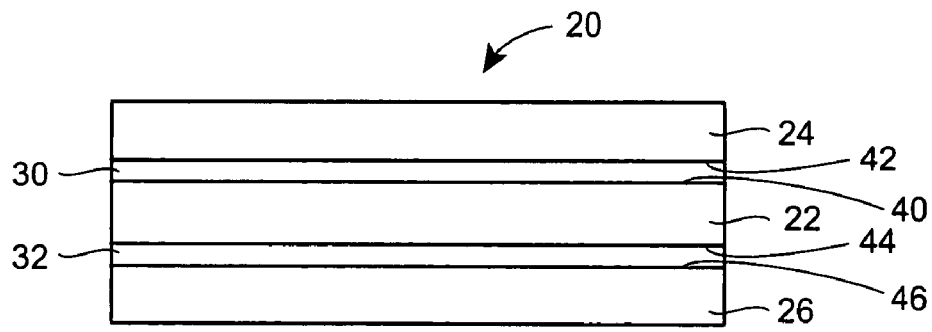
FIG. 1A is a side view of a first embodiment of a stretch laminate according to the present disclosure.

As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

The terms "adhesively bonded" or "adhesively laminated" refers to a laminate wherein an adhesive is used to bond the elastomer member to the nonwoven or nonwovens.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "diaper" refers to an absorbent article generally worn by infants and incontinent persons about the lower torso and having the general form of a sheet, different portions of which are fastened together to encircle the waist and the legs of the wearer.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "disposed" is used to mean that an element(s) is formed (joined and positioned) in a particular place or position as a unitary structure with other elements or as a separate element joined to another element.

The terms "interior" and "exterior" may refer respectively to the location of an element that is intended to be placed against or toward the body of a wearer when an absorbent article is worn and the location of an element that is intended to be placed against or toward any clothing that is worn over the absorbent article. "Interior" and "exterior" may also refer to a particular orientation of elements relative to each other, without specific or special reference to the wearer. Synonyms for "interior" and "exterior" include, respectively, "inner" and "outer", as well as "inside" and "outside". Also, when an absorbent article is oriented such that its interior faces upward, for example, when it is laid out in preparation for setting the wearer on top of it, synonyms include "upper" and "lower" and "top" and "bottom", respectively.

The term "joined" refers to configurations whereby an element is directly secured to another element by attaching the element directly to the other element, and configurations whereby an element is indirectly secured to another element by attaching the element to intermediate member(s) which in turn are attached to the other element.

The term "lateral" or "transverse" refers to a direction running at a 90 degree angle to the longitudinal direction and includes directions within ±45° of the lateral direction.

The term "longitudinal" refers to a direction running parallel to the maximum linear dimension of the article and includes directions within ±45° of the longitudinal direction.

The term "macroporous" refers to materials having pores too large to effect capillary transport of fluid, generally having pores greater than about 0.5 mm in diameter and, more specifically, having pores greater than about 1.0 mm in diameter. The term "microporous" refers to materials which are capable of LaPlace pressures greater in magnitude than approximately 10 kPa.

The term "pant" or "pants" refers to an absorbent article generally worn by infants and incontinent persons about the lower torso and having the general form of a pair of short pants that can be applied or removed from the wearer without unfastening. A pant may be placed in position on the wearer by inserting the wearer's legs into the leg openings and sliding the pant into position about the wearer's lower torso. While the term "pant" is used herein, pants are also commonly referred to as "closed diapers", "prefastened diapers", "pull-on diapers", "training pants" and "diaper-pants".

The term "refastenable" refers to the property of two elements being capable of releasable attachment, separation, and subsequent releasable reattachment without substantial permanent deformation or rupture.

The terms "releasably attached," "releasably engaged," and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

Stretch Laminate and Method of Fabrication

Figure 1B:
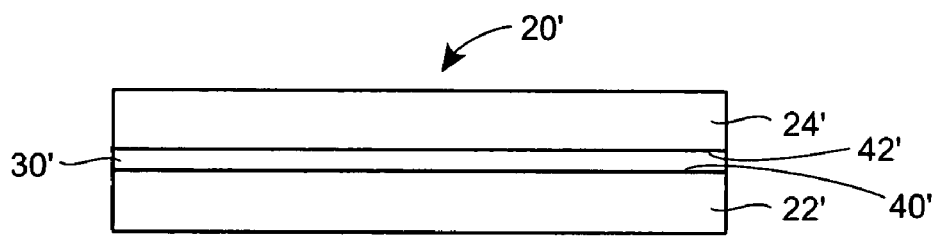
FIG. 1B is a side view of a second embodiment a stretch laminate according to the present disclosure.

FIG. 1A illustrates an embodiment of a stretch laminate 20 according to the present disclosure. According to this embodiment, the laminate 20 may include three layers: a first, or inner, layer 22 and second and third, or outer, layers 24, 26. However, according to other embodiments, the laminate 20' may include only two layers, the first and second layers 22', 24', as shown in FIG. 1B.

The first, second and third layers 22, 24, 26 may be attached to each other. For example, an adhesive may be disposed between the layers 22, 24, 26, as shown at 30, 32. As will be recognized, the adhesive 30 may be initially disposed either on a surface 40 of the layer 22 or a surface 42 of the layer 24, and the adhesive 32 may be similarly initially disposed either on an opposite surface 44 of the layer 22 or a surface 46 of the layer 26. As assembled, the adhesive 30 attaches the surface 40 (and thus the layer 22) to the surface 42 (and thus the layer 24), and the adhesive 32 attaches the surface 44 (and thus the layer 22) to the surface 46 (and thus the layer 26).

While the layers 22, 24, 26 appear to overlie each other completely, this need not be the case in all embodiments. For example, the layers 24, 26 may extend beyond the layer 22, and may be attached one to the other where the layers 24, 26 extend beyond the layer 22; alternatively, the layers 24, 26 may not extend to the limits of the layer 22. Also, while the adhesive 30, 32 appears as a continuous layer in the Figure, the adhesive 30, 32 may be applied as a continuous layer or in a discontinuous pattern (such as a pattern of lines, spirals, or spots). Further, alternative attachment mechanisms may include heat bonding, pressure bonding, ultrasonic bonding, dynamic mechanical bonding, or any other suitable attachment mechanism or combinations of these attachment mechanisms.

According to the present disclosure, the inner layer 22, or core, may include an elastomer film. Exemplary elastomer films may include those elastomer films that have an engineering tensile strength greater than about 14 MPa, as measured at an engineering strain rate of about 600/s. In certain embodiments, the engineering tensile strength may be greater than about 20 MPa, as measured at an engineering strain rate of about 600/s. These exemplary elastomer films may also have an engineering tensile strength of greater than about 7 MPa, as measured at a strain rate of about 600/s, for a notched high-speed test, as described in greater detail below. In certain embodiments, the engineering tensile strength may be greater than about 15 MPa, as measured at an engineering strain rate of about 600/s for the notched high-speed test. At the present time, it is believed that high strength at high speeds, whether that strength is measured with a notch in the specimen, may be significant in selecting suitable elastomer films. However, it may be that elastomer films that exhibit high strength at high speeds both in the notched and unnotched tests may have an even greater suitability for use in stretch laminates than elastomers that exhibit high tensile strength in either the notched or the unnotched test. It may also be that the engineering tensile strength in the notched test is more significant in selecting an appropriate material than the unnotched, or plain, specimen test.

Exemplary elastomer films may include those with skins, and those that are skinless. However, while skins may be helpful at avoiding blocking, it is believed that they do not contribute substantially to the film's ability to avoid damage during activation at the layer ratios relevant for good elastomeric properties. Instead, as explained in greater detail below, it is believed that the elastomer's mechanical properties (for example, engineering strength) are of primary concern for high speed mechanical integrity in the context of activation.

An exemplary elastomer film meeting the tensile strength requirements provided above may be made according to the following exemplary method. An UltraGlide twin screw extruder, commercially available from Berstorff GmbH of Hannover, Germany (with 25.4 mm diameter and L:D=32) was used 253-128 resin commercially available from GLS Composites Distribution Group of McHenry, Ill. The extruder was fitted with a vibratory feeder to deliver the resin pellets to the extruder's feed throat at a constant rate. The extrusion temperatures were set at about 300° F. for the first extrusion zone and about 430° F. for the last extrusion zone and the die, and selected for the middle zones to give a suitable upward temperature ramp profile. The screw speed was about 100 rpm. The extruder was fitted with a 6 inch (15.2 cm) wide film die, and the film was cast directly onto release paper on a suitable film take-up apparatus.

The outer layers 24, 26 may be of a nonwoven material, such as SM (spunbond meltblown), SMS (spunbond meltblown spunbond), and SMMS (spunbond meltblown meltblown spunbond) nonwovens. The nonwoven materials may also include carded nonwovens, such as those specially designed and manufactured to be compatible with the activation (or ring-rolling) process. For that matter, the spunbounds may also be specially designed and/or manufactured to be compatible with the activation process. However, it is believed that through the use of the elastomer layer according to the present disclosure, greater flexibility in the design choices may be achieved. For example, spunbounds may be selected for applications where only carded nonwovens were used in the past, or thinner elastomer layers may be used with the carded nonwovens. Other improvements in design flexibility will also be recognized by the skilled practitioner.

The basis weight of the nonwoven material may be less than about 25 gsm. In fact, according to certain embodiments, the basis weight may be less than about 22 gsm. In other embodiments, the basis weight may be less than about 20 gsm. In still other embodiments, the nonwoven material may have a basis weight of less than about 18 gsm.

The adhesive 30, 32 may be selected from those adhesives known to provide suitable attachment between the film 22 and the nonwoven layers 24, 26. According to one embodiment, the adhesive may be the adhesive commercially available from an H2031 adhesive commercially available from Bostik Inc. of Middleton, Mass. One characteristic of this adhesive is that, at 23C, this adhesive has significant pressure-sensitive character useful for making laminate by hand. However, this adhesive is also suitable for use in fabricating laminates from the films and nonwovens listed above using conventional laminate manufacturing equipment, such equipment being well known in the art.

An exemplary method of fabricating a laminate using the films, nonwovens and adhesives listed above is as follows. The adhesive 30 is originally disposed on a sheet of release paper. The adhesive 30 may be transferred to one side 42 of the nonwoven 24 by placing the sheet of nonwoven 24 on the adhesive 30, and then applying sufficient pressure to the nonwoven 24, with a hand roller, for example. The adhesive 30 and nonwoven 24 are then gradually peeled off of the release paper, and applied to the surface 40 of the film 22. This procedure may be repeated to attach the other nonwoven 26 to the adhesive 32, and then the nonwoven 26 and adhesive 32 to the surface 44 of film 22. Once the layers 22, 24, 26 are assembled, a hand roller, for example, may be used to apply moderate pressure to the laminate 20 to give laminate 20 adequate peel strength (about 1-2 N/cm). It will be recognized that these steps may be performed on conventional fabrication equipment, according to the knowledge of those of skill in the art.

The laminate may then be subjected to a process sometimes referred to as "ring-rolling." During the ring rolling process, corrugated interengaging rolls are used to permanently elongate the substrate to reduce its resistance to stretch. The resulting laminate has a greater degree of stretchability in the portions that have been subjected to the ring rolling process. Thus, this secondary operation provides additional flexibility in achieving stretch properties in localized portions of the stretch composite. Methods for imparting stretchability to an extensible or otherwise substantially inelastic material by using corrugated interengaging rolls which incrementally stretch in the machine or cross-machine direction and permanently deform the material are disclosed in U.S. Pat. Nos. 4,116,892; 4,834,741; 5,143,679; 5,156,793; 5,167,897; 5,422,172; and 5,518,801. In some embodiments, the intermediate structure may be fed into the corrugated interengaging rolls at an angle with respect to the machine direction of this secondary operation. Alternatively, the secondary operation may employ a pair of interengaging grooved plates applied to the intermediate structure under pressure to achieve incremental stretching of the intermediate structure in localized portions.

It is believed that an elastomer of the present disclosure, which exhibits high tensile strength at high speeds (which may be expressed in the form of high strain rates), may improve the performance characteristics of the stretch laminate 20 made using the elastomer, leading to potential reductions in the cost of the stretch laminate. For example, it is theorized that the formation of mechanical damage (for example, ruptures and holes) during activation may be inhibited or limited by an elastomer that exhibits a high tensile strength at high speeds over the relevant range of strains. In this regard, it will be readily recognized that a high strength material that breaks at a strain lower than that experienced by the laminate during the ring-rolling procedures, for example, will not be acceptable. Provided the material's engineering strain at break is sufficiently large to accommodate the ring-rolling process, it is believed that elastomer tensile strength may be the primary criterion for avoidance of the onset of film damage (for example, rupture or holes). The reduction in the cost of a laminate using such a high strength elastomer, may come about in a number of different ways. For example, if the laminate (in particular, the elastomer) is more resistant to hole formation, it may be possible to use a smaller gauge of elastomer film for a particular laminate, resulting in reduced material costs. In a similar vein, use of the elastomer according to the present disclosure may limit the necessity of using the larger gauge elastomer film that might otherwise be required for a particular application. As another alternative, nonwovens that are not carded, such as spunbounds that may be less expensive than carded nonwovens, may be used for a particular applications where the use of such nonwovens was not typically made if an elastomer film according to the present disclosure is used.

Tensile Testing Methods and Results

Exemplary methods of testing an elastomer to determine if it meets the strength criterion follow. In particular, the elastomers were tested for tensile strength, which may be expressed as the maximum engineering stress experienced by a specimen before breakage.

The exemplary methods of testing for the strength criterion were performed using an 810 Material Testing System, commercially available from MTS Systems Corporation of Eden Prairie, Minn. In particular, the system used was equipped with a servohydraulic actuator capable of speeds exceeding 5 m/s after 28 mm of travel, and approaching 6 m/s after 40 mm of travel. The system was also fitted with a 50 lb. Kistler force transducer, signal conditioned with a Kistler 5010 dual mode amplifier.

Plain and notched specimens were prepared for testing. In this regard, it was observed that that holes forming in an elastomer layer of a stretch laminate may be considered as a flaw in the material. Consequently, it is believed that a notch in the specimen provides a suitable simulation of hole formation in the specimen, and that the tensile strength of the notched specimen may provide useful information in setting a criterion to limit hole formation in the elastomer layer.

As to both the plain and notched specimens, the film was initially placed between two sheets of paper. A sharp blade, such as an XACTO knife commercially available from Hunt Corporation of Philadelphia, Pa., and a metal straight edge were then used to cut a specimen that was 19 mm wide by approximately 16.5 mm long from the film. The film's machine direction and transverse direction (also known as the cross-machine direction) coincided with the 19 mm and 16.5 mm dimensions, respectively, such that the specimen would be deformed along its transverse direction during the testing. The specimen's 16.5 mm dimension was measured with a scale to the nearest 0.2 mm and was weighed on a 4-place lab balance.

In regard to the notched specimens, a 1 mm notch was cut in the edge of the specimen perpendicular to the edge of the specimen. The notch was cut using an XACTO-knife and a steel plate machined with a suitable guide formed therein. Each notch was measured with a magnifier (7×) and appropriate reticle, and only specimens with notches that fell within the range of 1 mm±0.1 mm were used in the testing.

Figure 2:
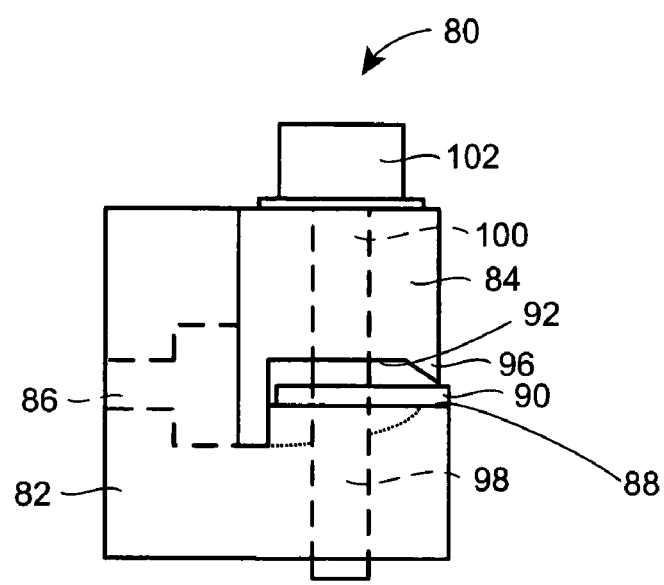
FIG. 2 is a schematic of a grip that may be used in testing performed on specimens of an elastomer to determine if the elastomer meets a strength criterion.

According to the exemplary testing methods, the system was equipped with a set of custom-fabricated grips 80, as illustrated in FIG. 2, for mounting the specimens thus prepared. The grip 80 has a stationary member 82 and a moveable member 84. The stationary member 82 has a recess 86 formed therein to receive a bolt that may be attached to the load cell (not shown) of the system. The stationary member 82 also has a surface 88 to which a mounting mat 90 is attached, the mounting mat 90 being formed of urethane rubber, for example. The moveable member 84 has a surface 92 that faces the surface 88. An apex 96 depends from the surface 92, which apex 96 may have a radius of about 1 mm. The moveable member 84 each has a passage 100 through which a bolt 102 is disposed. The passage 98 defined in the stationary member 82 may be threaded, such that the threads of the bolt 102 engage the threads of the passage 98 to hold the moveable member 84 in a relatively fixed relationship to the stationary member 82 with an edge of the specimen disposed between the apex 96 and the mounting mat 90 to provide line contact with the specimen.

The specimens were mounted in the custom-fabricated grips as follows. The grips were first moved to a grip separation (i.e., the distance between the lines of contact between specimen and grip surface) of 10 millimeters. The specimen was then mounted in the grips. Optionally, a powder, such as corn starch, and a thin piece of tape may be used during the mounting process. The powder may be used to limit the specimen's tack, while the tape may be used to help hold the specimen straight and flat while mounting in grips. If tape is used, it is recommended that the tape remain behind the lines of gripping so that the tape does not interfere with the specimen's gauge during the test. The grips were then moved closer together to introduce considerable slack into the specimen, but not so much that the grips interfered with each another.

Figure 3:
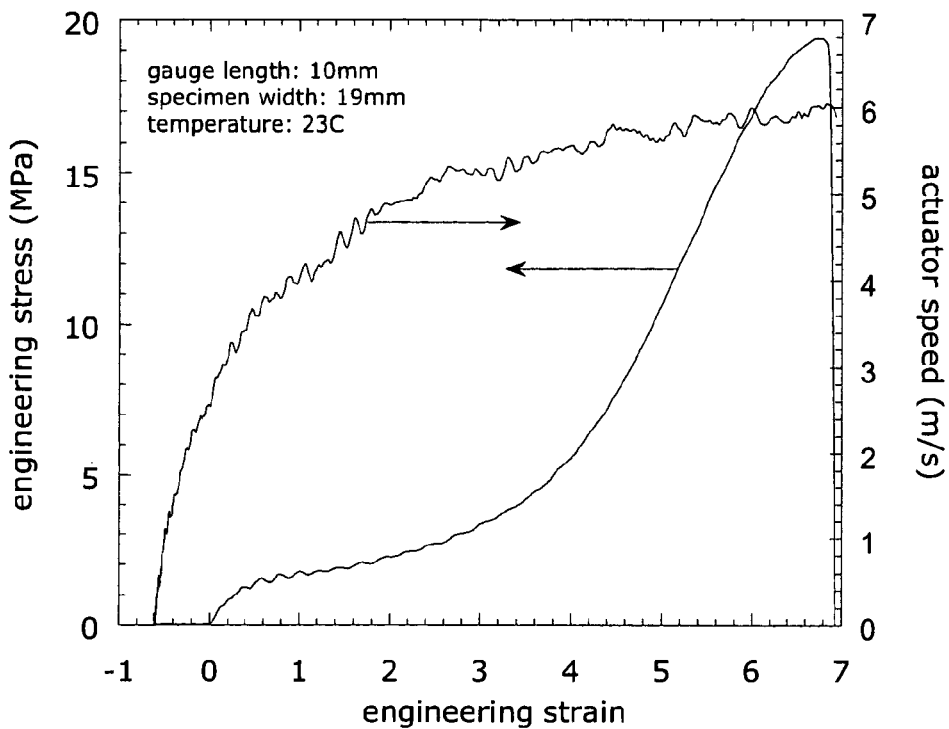
FIG. 3 is a graph illustrating a deformation regimen that may be used in testing performed on specimens of an elastomer to determine if the elastomer meets a strength criterion.

The specimen, so mounted, may be tested as follows, although other methods may be used. Actuator movement was commenced according to the deformation regimen shown in FIG. 3 at room temperature (23C) and using a load cell selected according to the operator's experience. The gauge length (the distance between lines of grip contact when the undeformed specimen is mounted in the grips) was 10 mm for all specimens tested. Recording of force and actuator displacement data during the test was achieved using a Nicolet Integra oscilloscope. Typical data acquisition frequency under experimental conditions such as described above may be 40 kHz.

Results

Figure 4:
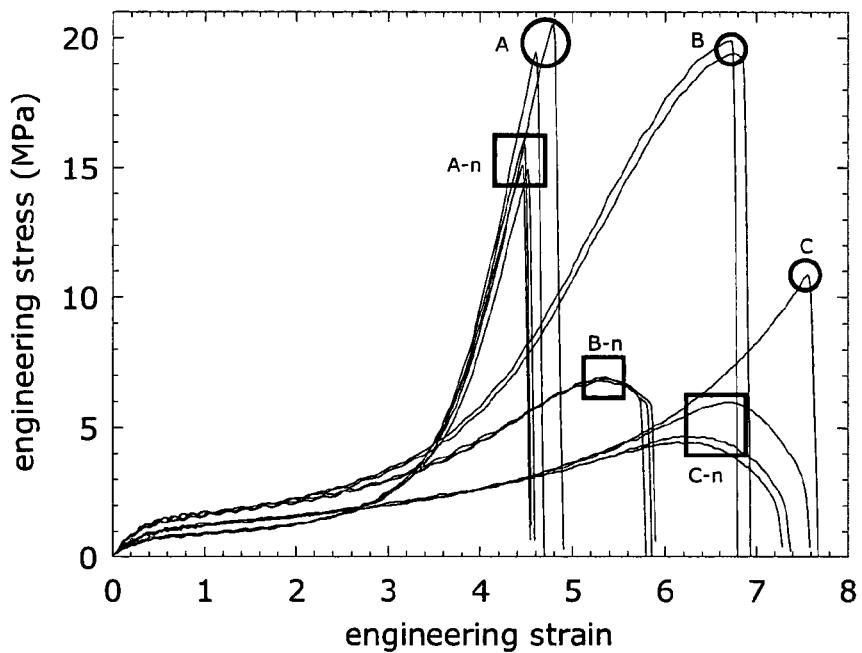
FIG. 4 is a graph illustrating results of testing performed on specimens of several elastomers to determine if those elastomers meet a strength criterion.

The results of the testing have been summarized herein, and in the graph of FIG. 4. The results are expressed in terms of engineering stress, engineering strain, and engineering strain rate. In this regard, the following relationships are noted.

Engineering stress σ (expressed in MPa) may be calculated using the equation:

$$\sigma = 10^{-6} * \frac{F}{A}$$

where F is force (expressed in Newtons) and A is the specimen's cross-sectional area (expressed in $m^2$). To perform this calculation, the specimen's cross-sectional area was itself calculated according to the following equation:

$$A = \frac{m}{l * \rho}$$

where m is mass (expressed in kg), l is dimension along the direction of deformation (expressed in m), and ρ is density (in $kg/m^3$). The mass and length measurements of the individual specimen were taken as described above. The density was taken as 950 or 920 $kg/m^3$ for elastomers comprised predominantly of non-hydrogenated and hydrogenated SBC, respectively, according to historical norms for similar elastomers as determined by methods known by those skilled in the art (such as density gradient columns, or application of Archimedes principle). It is believed the density values may be accurate to within about 5% for the specimens described herein.

Engineering strain ε (unitless) is defined as $$\varepsilon = \frac{L - L_0}{L_0} = \frac{z}{L_0}$$

where $L_0$ is gauge length—the distance between lines of grip contact when the undeformed specimen is mounted in the grips (expressed in m), L is grip position—the distance between lines of grip contact during the tensile test (expressed in m), and z is displacement—defined as $z = L - L_0$ (expressed in m).

Engineering strain rate (expressed in $s^{-1}$) is the first time derivative of engineering strain. Thus, the strain rate may be calculated according to:

$$\frac{d\varepsilon}{dt} = \frac{v}{L_0}$$

where v is the speed at which one grip moves relative to the other (expressed in m/s), and $L_0$ is gauge length (express in m).

Six different elastomer films (identified as films A-F herein) were tested for tensile strength. The films had basis weights of between about 80 and about 100 gsm. The films were prepared according to two different methods.

Five of the films (A-E) were prepared according to the following method: An UltraGlide twin screw extruder, commercially available from Berstorff GmbH of Hannover, Germany (with 25.4 mm diameter and L:D=32) was used. The extruder was fitted with a vibratory feeder to deliver the resin pellets to the extruder's feed throat at a constant rate. The extrusion temperatures were set at about 300° F. for the first extrusion zone and about 430° F. for the last extrusion zone and the die, and selected for the middle zones to give a suitable upward temperature ramp profile. The screw speed was about 100 rpm. The extruder was fitted with a 6 inch (15.2 cm) wide film die, and the film was cast directly onto release paper on a suitable film take-up apparatus.

The sixth film (F) was prepared according to the following method: A small amount of resin was compression molded to a thickness of 150-200 micrometers using conventional equipment. The resin was disposed between layers of polytetrafluoroethylene (PTFE) film. The assembly thus formed then was disposed between plates held at about 450° F. for a dwell time of about 30 seconds.

Film A was formed using a 253-128 resin commercially available from GLS Composites Distribution Group of McHenry, Illinois. Film B was formed using about 83% by weight of a Vector 4211 resin commercially available from Dexco Polymers LP of Plaquemine, La., and about 17% by weight of a PS3190 resin commercially available from Nova Chemicals Corp. of Calgary, Canada. Film C was formed using just the Vector 4211 resin. Film D was formed using about 83% by weight of a D1164 resin commercially available from Kraton Polymers LLC of Houston, Tex., and about 17% by weight of the PS3190 resin. Film E was formed using a 148-089 resin commercially available from GLS Composites Distribution Group. Film F was formed using a PG-C-016 resin commercially available from Kuraray America Inc. of New York, N.Y.

The results of the testing of all six films are summarized in the table below, form both plain (unnotched) and notched specimens. Additionally, the test results for plain and notched specimens of films A-C are also illustrated in FIG. 4.

| Tensile Strength Results | | |
| --- | --- | --- |
| Film Identifier | Plain Specimen Tensile Strength (in MPa) | Notched Specimen Tensile Strength (in MPa) |
| A | 20.0 | 15.4 |
| B | 19.6 | 6.9 |
| C | 10.6 | 5.0 |
| D | 19.3 | 7.2 |
| E | 15.5 | 4.6 |
| F | 15.9 | 14.0 |

It is believed at the present time that the elastomer film with the highest engineering tensile strengths, both for the plain and the notched tests, would best exhibit the desired improvements in design flexibility discussed above: i.e., elastomer film A. However, it is also believed that suitable improvements in design flexibility may be achieved with elastomer films B, D, and F, for example.

Comparative Testing Methods and Results

Films A-C, tested above for tensile strength, were also used for comparative testing involving activation of laminates formed using the elastomer films. Exemplary methods of testing follow.

Figure 5:
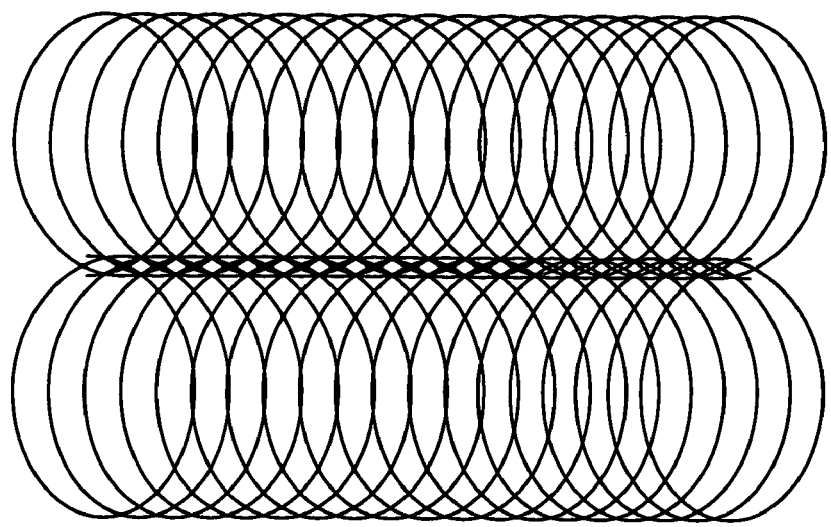
FIG. 5 is a schematic of an adhesive pattern used to join elastomer and nonwoven layers of stretch laminates used in comparative testing.

Three-ply laminates were prepared using the film of interest (film A, B, or C) prepared with a basis weight of between about 48 and about 52 gsm, a H0101711 non-woven material having a basis weight of about 17 gsm and commercially available from Fibertex A/S of Aalborg, Denmark, and an H2031 adhesive commercially available from Bostik Inc. of Middleton, Mass. with a basis weight selected to provide a laminate bond strength of about 1-2 N/cm. The adhesive was applied to a sheet of silicone release paper in a spiral pattern at the desired basis weight, which ranged between about 4.7 and abut 9.3 gsm. In particular, ITW D70 nozzles were used, with flowrate, nozzle height, air and temperature settings chosen to give suitable adhesive spirals. The release paper was mounted on an X-Y table programmed to raster and index so that the adhesive spirals have a suitable spatial relationship with one another, for example, slight overlap (see FIG. 5). The adhesive was transferred from the release paper to a first layer of the nonwoven by disposing the nonwoven layer onto the adhesive. A hand roller was used to apply pressure needed to the adhesive and nonwoven to allow both to be peeled from the release paper. The film was then disposed on the adhesive, and the roller applied. This procedure was repeated to apply a second nonwoven layer to the film's other surface. After the both nonwoven layers were attached to the film, the hand roller was used to apply further pressure over several repetitions, until the laminate bond strength "saturated," i.e., did not increase significantly with additional rolling or pressure.

Figure 6:
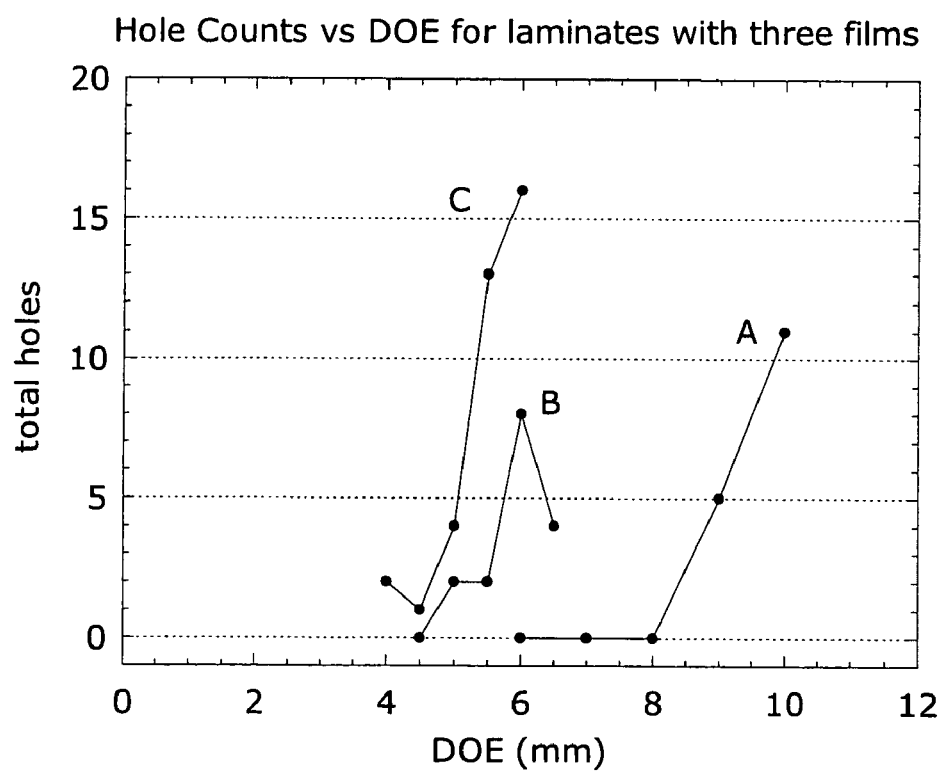
FIG. 6 is a graph illustrating results of comparative testing performed on specimens of stretch laminates made with and without an elastomer that meets the strength criterion set out herein.

Sheets of the laminate having dimensions of about 150 mm long by about 80 mm wide (in the machine and transverse directions, respectively) underwent the activation processing. Specifically, the sheets were mounted in a press such as the one described in U.S. Pat. Nos. 6,843,134 and 6,915,700 and U.S. Patent Publication No. 2004/0177709. The sheets were oriented so that the transverse direction of the sheet coincided with the tooth direction of the press. The following parameters were used:

Roll Diameter: 152.4 mm
Web Speed: 2.75 m/s
Tooth Tip Radius: 0.102 mm
Tooth Pitch: 3.81 mm
Tooth Height: 25.3 mm
Teeth: 23
Degree of Engagement: 4 mm to 11 mm The activated region of each specimen was about 100 mm long (as determined by the number of teeth used) by about 80 mm wide (as determined by the width of the sheet). After activation, each specimen was examined for ruptured locations (i.e., holes) in the film. The number of holes present were counted and have been summarized in the following table. Additionally, the test results for laminates made with Films A-C are also illustrated in FIG. 6.

Hole Counts

| Degree of Engagement (in mm) | Laminate with Film A | Laminate with Film B | Laminate with Film C |
| --- | --- | --- | --- |
| 4 | 0 | | 2 |
| 4.5 | 0 | 0 | 1 |
| 5 | 0 | 2 | 4 |
| 5.5 | 0 | 2 | 13 |
| 6 | 0 | 8 | 16 |
| 6.5 | 0 | 4 | |
| 7 | 0 | | |
| 8 | 0 | | |
| 9 | 5 | | |
| 10 | 11 | | |

It is believed that this testing method provides a quantitative measurement that may support the assessment reached above: that Film A provides a stretch laminate of performance better than stretch laminates made with the other films tested. It will be recognized that the stretch laminate made using the Film A elastomer exhibits fewer holes at higher degrees of engagement than laminates made using the Film B and Film C elastomers. It is believed that this may permit a lesser gauge (thickness) of Film A to be used for a given application that that of Films B or C, or that a greater range of nonwoven choices may be made for a laminate wherein the Film A elastomer is used than may be possible with the Film B and C elastomers. It is also believed that the test results show the difference in performance between laminates made using Film B relative to those laminates made using Film C, for example.

Exemplary Absorbent Article

Having thus described the stretch laminate according to the present disclosure and methods for its fabrication and testing, the use of the stretch laminate in an absorbent article is now discussed. While the use of the stretch laminate is suggested in regard to certain regions of the absorbent article, it will be recognized that the stretch laminate may be used in other regions as well.

Figure 7:
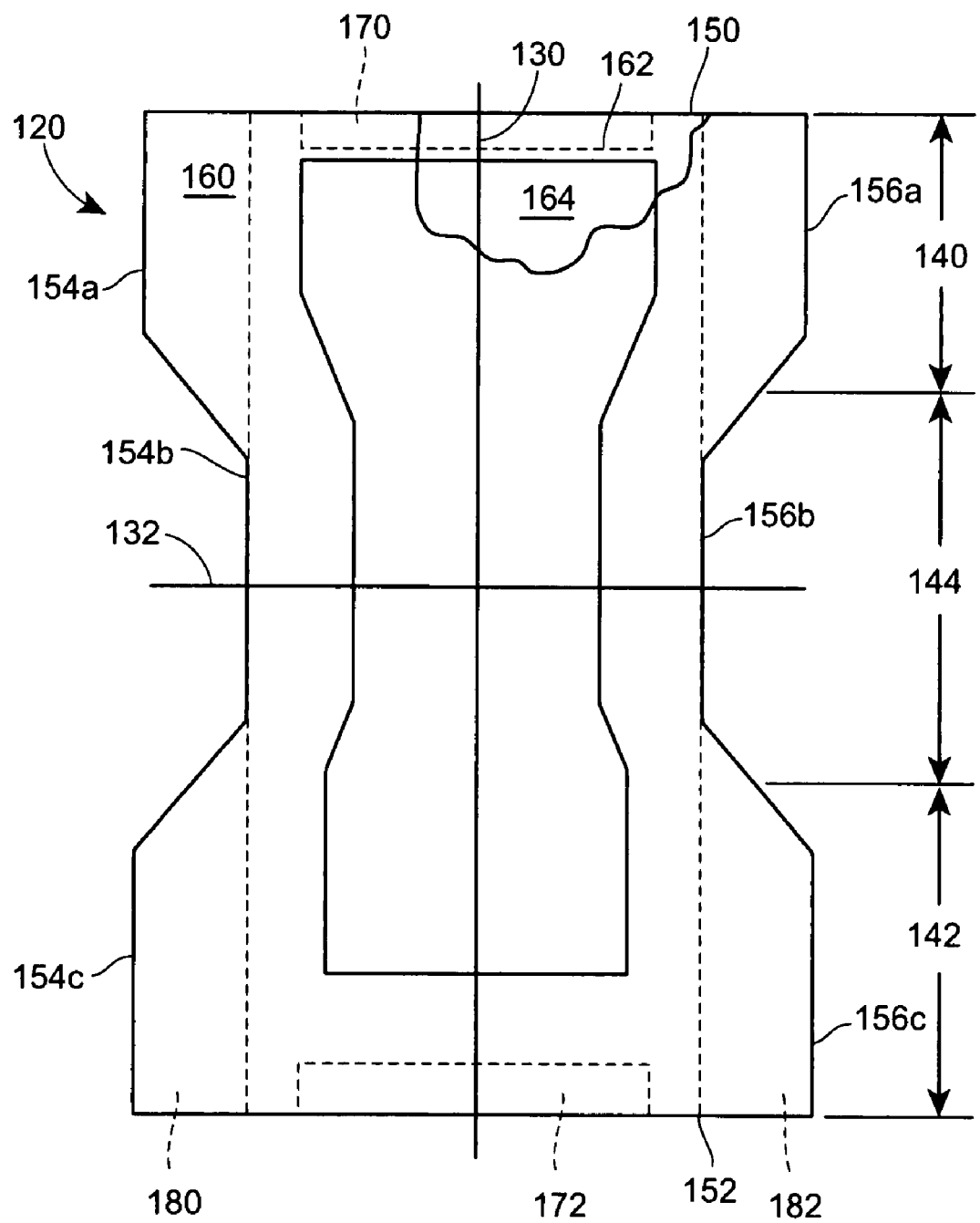
FIG. 7 is a plan view of an exemplary absorbent article including sections made of the stretch laminate of FIGS. 1A, 1B, with a section of a topsheet removed to expose an underlying absorbent core.

FIG. 7 is a plan view of an exemplary disposable absorbent article 120 in its flat, uncontracted state, i.e., without elastic-induced contraction. Portions of the article 120 have been cut away to more clearly show the underlying structure of the disposable absorbent article 120. As illustrated, the portion of the disposable absorbent article 20 that contacts the wearer faces the viewer (i.e., showing the interior or inner side of the article). The disposable absorbent article 120 has a longitudinal axis 130 and a transverse axis 132.

One end portion of the disposable absorbent article 120 is configured as a first waist region 140 of the disposable absorbent article 120. The opposite end portion is configured as a second waist region 142 of the disposable absorbent article 120. The waist regions 140 and 142 generally comprise those portions of the disposable absorbent article 120 which, when worn, encircle the waist of the wearer. The waist regions 140 and 142 may include elastic elements such that they gather about the waist of the wearer to provide improved fit and containment. An intermediate portion of the disposable absorbent article 120 is configured as a crotch region 144, which extends longitudinally between the first and second waist regions 140 and 142. The crotch region 144 is that portion of the disposable absorbent article 120 which, when the disposable absorbent article 120 is worn, is generally positioned between the legs of the wearer.

The disposable absorbent article 120 has a laterally extending first waist edge 150 in the first waist region 140 and a longitudinally opposing and laterally extending second waist edge 152 in the second waist region 142. The disposable absorbent article 120 has a first side edge 154 and a laterally opposing second side edge 156, both side edges extending longitudinally between the first waist edge 150 and the second waist edge 152. The portion of the first side edge 154 in the first waist region 140 is designated 154a, the portion in the crotch region 144 is designated 154b, and the portion in the second waist region 142 is designated 154c. The corresponding portions of the second side edge 156 are designated 156a, 156b, and 156c, respectively.

The disposable absorbent article 120 preferably comprises a water-permeable topsheet 160, a water-impermeable backsheet 162, and an absorbent assembly or core 164, which may be disposed between the topsheet 160 and the backsheet 162 with the topsheet 160 attached to the backsheet 162. The topsheet 160 may be fully or partially elasticized or may be foreshortened. Exemplary structures including elasticized or foreshortened topsheets are described in greater detail in U.S. Pat. Nos. 4,892,536; 4,990,147; 5,037,416; and 5,269,775, among others.

The absorbent article 120 may include at least one elastic waist feature 170 that helps to provide improved fit and containment. The elastic waist feature 170 may be intended to elastically expand and contract to dynamically fit the wearer's waist. The elastic waist feature 170 may extend at least longitudinally outwardly from at least one waist edge (for example, edge 150) of the absorbent article 150 and generally forms at least a portion of the waist region (for example, region 140) of the absorbent article 120. Diapers are often constructed so as to have two elastic waist features 170, 172, one (170) positioned in the first waist region 140 and one (172) positioned in the second waist region 142. Further, the elastic waist feature 170, 172 may be made of the stretch laminate 20 attached or joined to the backsheet 162. Alternatively, the elastic waist feature 170, 172 may be constructed as an extension of other elements of the absorbent article, such as the topsheet 160, the backsheet 162, or both the topsheet 160 and the backsheet 162 (for example, the topsheet 160 or backsheet 162 defines one of the layers 24, 26 of the laminate 20). Other elastic waist feature constructions are described in U.S. Pat. Nos. 4,515,595; 4,710,189; 5,151,092; and 5,221,274.

The absorbent article 120 may include side panels 180, 182 attached to the backsheet 162. One or more of the side panels 180, 182 may be made from the stretch laminate 20. This construction may provide a more comfortable and contouring fit by initially conformably fitting the absorbent article 120 to the wearer, and sustaining this fit throughout the time of wear well past when the absorbent article 120 has been loaded with exudates, insofar as the elasticized side panels 180, 182 allow the sides of the absorbent article 120 to expand and contract. The side panels 180, 182 may also provide more effective application of the absorbent article 120 because even if the caretaker pulls one elasticized side panel 180 farther than the other (182) during application, the absorbent article 120 will "self-adjust" during wear. While the absorbent article 120 preferably has the side panels 180, 182 disposed in the second waist region 142, the absorbent article 120 may be provided with side panels disposed in the first waist region 140, or in both the front waist region 140 and the second waist region 142.

Figure 8:
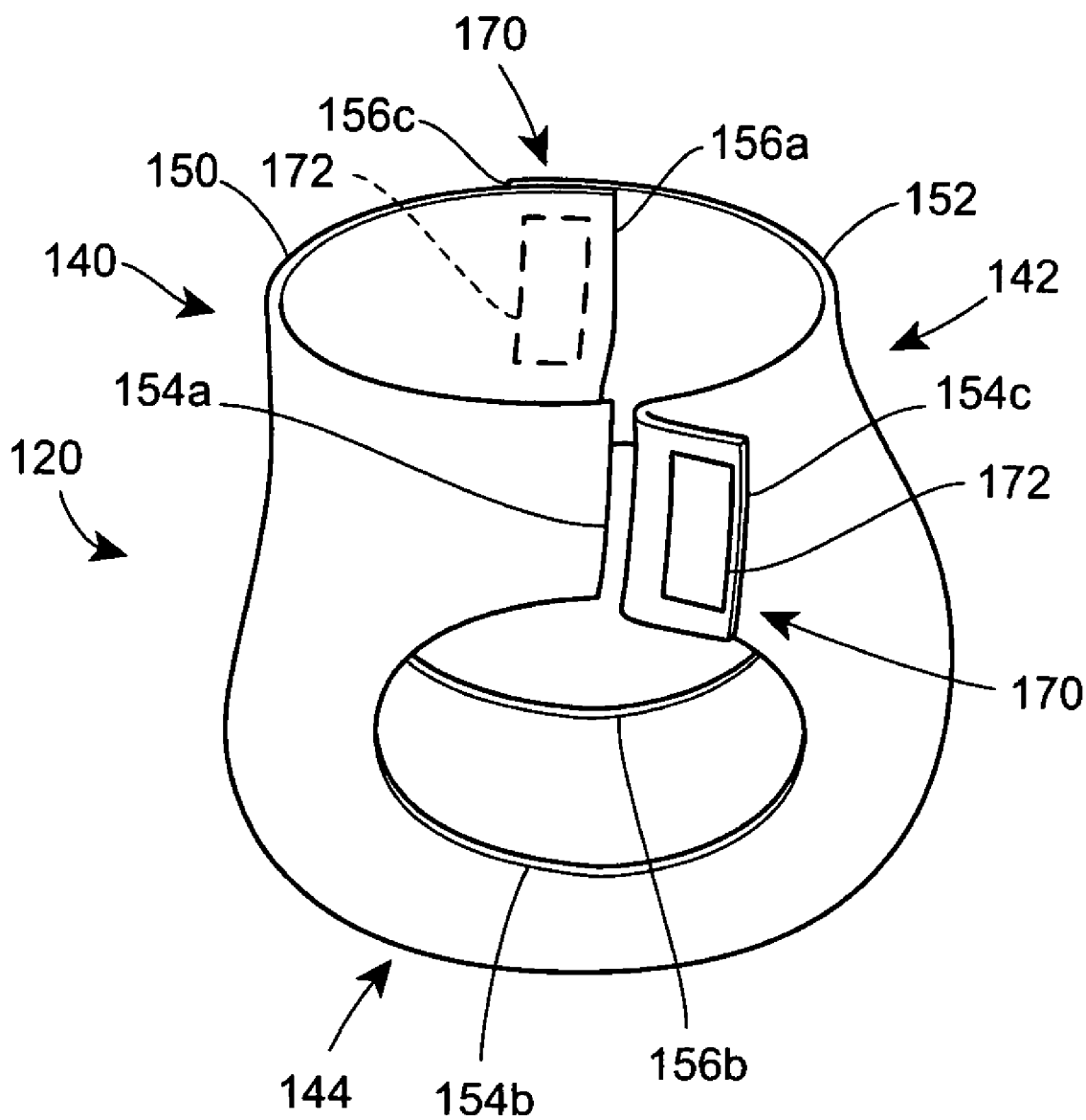
FIG. 8 is a perspective view of the absorbent article of FIG. 7 shown in its relaxed, contracted state, i.e., with the contraction induced by elastic members.

FIG. 8 illustrates the article illustrated in FIG. 7 configured to as it would be worn. The disposable absorbent article 120 may be sealed at the sides so as to be configured as illustrated in FIG. 8. However, the article 120 may instead include refastenable side seams 170 that can be used to fasten the waist regions 140, 142 together. According to one exemplary embodiment, the waist regions 140, 142 may be fastened at the sides to apply the article like a diaper. According to an exemplary embodiment, illustrated in FIG. 8, the side seams 170 may include fasteners 172 that can be used to configure the article like a pair of pull-on training pants or disposable pants.

As illustrated, the fasteners 172 may be disposed on the interior of the disposable absorbent article 120 in the second waist region 142 adjacent to the portion 154c of the first side edge 154 and adjacent to the portion 156c of the second side edge 156. The portion 154c of the side edge 154 is shown in an open condition, such as prior to closing and fastening or after being reopened. The portion 156c of the opposing side edge 156 is shown fastened, i.e., forming a pants configuration. In FIG. 8, the second waist region 142 overlaps the first waist region 140 when they are fastened together.

The fasteners 172 may be formed of any material and in any form that will releasably attach to the mating surface of the opposing waist region when pressed against it. For example, the primary fastening component may be a mechanical fastener that releasably engages with the mating surface, such as by means of a plurality of hooks engaging with loops formed by fibers in a nonwoven sheet. Alternatively, the primary fastening component may be an adhesive that releasably adheres to the mating surface. In fact, the fasteners may include tape tabs, hook and loop fastening components, interlocking fasteners such as tabs & slots, buckles, buttons, snaps, and/or hermaphroditic fastening components. Exemplary surface fastening systems are disclosed in U.S. Pat. Nos. 3,848,594; 4,662,875; 4,846,815; 4,894,060; 4,946,527; 5,151,092; and 5,221,274, while an exemplary interlocking fastening system is disclosed in U.S. Pat. No. 6,432,098. The fastening system may also include primary and secondary fastening systems, as disclosed in U.S. Pat. No. 4,699,622. Additionally exemplary fasteners and fastener arrangements, the fastening components forming these fasteners, and the materials that are suitable for forming fasteners are described in U.S. Published Application Nos. 2003/0060794 and 2005/0222546 and U.S. Pat. No. 6,428,526.

Still other variations are also possible. For example, the fasteners 172 may be disposed on the interior of the article 120 in the first waist region 140 such that the first waist region 140 overlaps the second waist region 142 when they are fastened together. As another example, the fasteners 170 may be disposed on the exterior of the article 20 rather than on the interior. As a further example, the fasteners 170 may be used with a specific mating fastener surface particularly suited for cooperation with the fasteners 170 (for example, a loop layer that works with a hook fastener, or a layer particularly treated to provide a suitable contacting surface for a specific adhesive).

Additional Variations to the Absorbent Article

In the alternative to the absorbent article 120 discussed above, various assemblies of topsheet 160, backsheet 162, and absorbent core 164 may be used. Additionally, the characteristics of the structures, the topsheet, for example, may be varied through the use of coatings, lotions, and the like. Further, in addition to the features described above, the disposable absorbent article 120 may include a variety of other features, such as slit openings, void spaces, leg cuffs, and the like to provide desired fit, containment, and aesthetic characteristics. Moreover, a transfer layer, which may also be referred to as an acquisition or distribution layer, or a sublayer may be disposed between the topsheet 160 and the core 164.

Thus, the topsheet, the backsheet, and the absorbent core may be assembled in the alternative in any of the well known configurations described in the following patent documents: U.S. Pat. Nos. 3,860,003; 5,151,092; 5,221,274; 5,554,145; 5,569,234; 5,580,411; and 6,004,306 (diapers) and U.S. Pat. Nos. 5,246,433; 5,569,234; 6,120,487; 6,120,489; 4,940,464; 5,092,861; 5,897,545; and 5,957,908 (pants).

The topsheet may be made from a wide range of materials, such as porous foams, reticulated foams, apertured plastic films, or woven or nonwoven materials of natural fibers (for example, wood or cotton fibers), synthetic fibers (for example, polyester or polypropylene fibers), or a combination of natural and synthetic fibers. If the topsheet includes fibers, the fibers may be spunbond, carded, wet-laid, meltblown, hydroentangled, or otherwise processed as is known in the art. One such material, including staple-length polypropylene fibers, is the P-8 material commercially available from Veratec, Inc., a Division of International Paper Company, of Walpole, Mass. Other alternative topsheets are described in U.S. Pat. Nos. 3,929,135; 4,324,246; 4,342,314; 4,463,045; and 5,006,394. Still other alternative topsheets may be made in accordance with U.S. Pat. Nos. 4,609,518 and 4,629,643. Films that may be used to make alternative topsheets may include DRI-WEAVE film commercially available from The Procter & Gamble Company of Cincinnati, Ohio and CLIFF-T film from Tredegar Corporation of Richmond, Va.

In certain embodiments, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in, for example, U.S. Pat. Nos. 4,988,344 and 4,988,345. A more detailed discussion of some suitable methods for incorporating a surfactant in the topsheet may be found in U.S. Statutory Invention Registration No. H1670. Alternatively, the topsheet may include an apertured web or film which is hydrophobic. This may be accomplished by eliminating the hydrophilizing treatment step from the production process and/or applying a hydrophobic treatment to the topsheet, such as a polytetrafluroethylene compound like the SCOTCHGUARD product commercially available from 3M Corporation of Minneapolis, Minn., or a hydrophobic lotion composition. In such embodiments, it is preferred that the apertures be large enough to allow the penetration of aqueous fluids like urine without significant resistance.

Other materials may be applied or incorporated into the topsheet. For example, any portion of the topsheet may be coated with a lotion as is known in the art. Examples of suitable lotions include those described in U.S. Pat. Nos. 5,607,760; 5,609,587; 5,635,191; 5,643,588; 5,968,025 and 6,716,441. The lotion may function alone or in combination with another agent as the hydrophobizing treatment described above. The topsheet may also include or be treated with antibacterial agents, some examples of which are disclosed in PCT Publication No. WO 95/24173. Still other possibilities will be recognized.

The backsheet may be made from a thin plastic film, such as a thermoplastic film, having a thickness of about 0.012 mm (0.5 mil) to about 0.051 mm (2.0 mils). Exemplary backsheet films include the CPC2 film commercially available from Tredegar Corporation of Richmond, Va. Alternatively, the backsheet may be made from breathable materials, which materials permit vapors to escape from the absorbent article while still preventing bodily exudates from passing therethrough. Exemplary breathable materials may include woven webs, nonwoven webs, microporous films (such as ESPOIR NO film commercially available from Mitsui Toatsu Co. of Japan and EXAIRE film commercially available from Tredegar Corporation of Richmond, Va.), and monolithic films (such as HYTREL blend P18-3097 film commercially available from Clopay Corporation of Cincinnati, Ohio). Other alternative breathable materials may include composite materials, such as film-coated nonwoven webs or the composite materials described in PCT Publication No. WO 95/16746 and U.S. Pat. Nos. 5,938,648; 5,865,823; and 5,571,096.

The absorbent core may exhibit a wide variety of characteristics. For example, the core may be made in a wide variety of sizes and shapes (for example, rectangular, hourglass, "T"-shaped, asymmetric, etc.). Further, the absorbent core may made from a wide variety of liquid-absorbent materials, such as those commonly used in disposable diapers and other absorbent articles, including comminuted wood pulp, which is generally referred to as airfelt. Other alternative absorbent materials may include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. The configuration and structure of the absorbent core may also be varied: for example, the absorbent core(s) or other absorbent structure(s) may have varying caliper zones, hydrophilic gradient(s), superabsorbent gradient(s), or lower average density and lower average basis weight acquisition zones. Exemplary structures for use as the absorbent core may include those in U.S. Pat. Nos. 4,610,678; 4,673,402; 4,834,735; 4,888,231; 5,137,537; 5,147,345; 5,342,338; 5,260,345; 5,387,207; and 5,625,222.

The backsheet may be joined to the topsheet, the absorbent core or any other element of the absorbent article. In this fashion, the backsheet and the topsheet may be joined directly to each other in some locations and indirectly together in other locations, for example, by directly joining them to one or more other elements of the absorbent article 120. The attachment may be formed by any of a variety of attachment methods or mechanisms. For example, the attachment methods or mechanisms may include a uniform continuous layer of adhesive, a patterned layer of adhesive, or an array of separate lines, spirals, or spots of adhesive. One possible attachment mechanism includes an open pattern network of filaments of adhesive, as in U.S. Pat. No. 4,573,986. Another suitable attachment mechanism includes several lines of adhesive filaments which are swirled into a spiral pattern, as in U.S. Pat. Nos. 3,911,173; 4,785,996; and 4,842,666. Other adhesives which may be used are the HL-1620 and HL-1358-XZP adhesives commercially available from H. B. Fuller Company of St. Paul, Minn. Further alternative attachment mechanisms may include heat bonding, pressure bonding, ultrasonic bonding, dynamic mechanical bonding, or any other suitable attachment mechanism or combinations of these attachment mechanisms.

The topsheet may comprise one or more apertures to ease penetration of exudates therethrough, such as urine and/or feces (solid, semi-solid, or liquid). In sizing the primary aperture, it is appropriate to consider that, if the primary aperture is too small, the waste may not pass through the aperture, either due to poor alignment of the waste source and the aperture location or due to fecal masses having a diameter greater than the aperture. Likewise, if the aperture is too large, the area of skin that may be contaminated by "rewet" from the article is increased. Typically, the aperture should have an area of between about 10 cm² and about 50 cm². The aperture preferably has an area of between about 15 cm² and 35 cm².

Moreover, the absorbent article may also include pockets for receiving and containing waste, spacers which provide voids for waste, barriers for limiting the movement of waste in the article, compartments or voids which accept and contain waste materials deposited in the absorbent article 120, and the like, or any combinations thereof. Examples of pockets and spacers for use in absorbent products are described in U.S. Pat. Nos. 5,514,121; 5,171,236; 5,397,318; 5,540,671; 6,168,584; 5,306,266; and 5,997,520. Examples of compartments or voids are disclosed in U.S. Pat. Nos. 4,968,312; 4,990,147; 5,062,840; and 5,269,755. Exemplary structures, including elasticized or foreshortened topsheets, to provide a void space between the topsheet and the core are described in more detail in U.S. Pat. Nos. 4,892,536; 4,990,147; 5,037,416; and 5,269,775. Examples of suitable transverse barriers are described in U.S. Pat. Nos. 5,554,142 and 5,653,703; and PCT Publication No. WO 94/14395. Examples of other structures especially suitable for management of low viscosity feces are disclosed in U.S. Pat. Nos. 5,941,864; 5,977,430 and 6,013,063.

The absorbent article may include leg cuffs which provide improved containment of liquids and other body exudates. Leg cuffs may also be referred to as leg bands, side flaps, barrier cuffs, or elastic cuffs. Suitable cuffs may be described in U.S. Pat. Nos. 3,860,003; 4,808,178; 4,909,803; 4,695,278; and 4,795,454. In some embodiments, it may be desirable to treat all or a portion of the leg cuffs 32 with a lotion.

The absorbent article may also include a sublayer disposed between the topsheet and the backsheet. The sublayer may be any material or structure capable of accepting, storing or immobilizing bodily exudates. Thus, the sublayer may include a single material or a number of materials operatively associated with each other. Further, the sublayer may be integral with another element of the diaper or may be one or more separate elements joined directly or indirectly with one or more elements of the diaper. Further, the sublayer may include a structure that is separate from the core or may include or be part of at least a portion of the core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes XPL-7124 mechanical fastening loop landing element, having an uncompressed thickness of about 1.5 millimeters, commercially available from the 3M Corporation of Minneapolis, Minn. Another embodiment includes a 6 denier, crimped and resin-bonded nonwoven highloft, having a basis weight of 110 grams per square meter and an uncompressed thickness of 7.9 millimeters, commercially available from The Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present invention. To the extent that any meaning or definition of a term in this disclosure conflicts with any meaning or definition of the term in a document incorporated by reference, the meaning or definition assigned to the term in this disclosure shall govern for this disclosure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A stretch laminate comprising:
    a first layer comprising an elastomer film, the first layer having a surface; and
    a second layer comprising a nonwoven material, the second layer having a basis weight of less than about 25 gsm and a surface that is attached to the surface of the first layer,
    the elastomer film having an engineering tensile strength, at an engineering strain rate of about 600/s, of at least one of about greater than about 14 MPa for a plain specimen or about greater than about 7 MPa for a notched specimen, wherein an assembly comprising the first layer attached to the second layer is activated, wherein activating the assembly comprises ring rolling the assembly using corrugated interengaging rolls.

2. The stretch laminate according to claim 1, wherein the elastomer film has an engineering tensile strength, at an engineering strain rate of about 600/s, of greater than about 20 MPa for a plain specimen.

3. The stretch laminate according to claim 1, wherein the elastomer film has an engineering tensile strength, at an engineering strain rate of about 600/s, of greater than about 15 MPa for a notched specimen.

4. The stretch laminate according to claim 1, wherein the elastomer film has an engineering tensile strength, at an engineering strain rate of about 600/s, of greater than about 20 MPa for a plain specimen and of greater than about 15 MPa for a notched specimen.

5. The stretch laminate according to claim 1, wherein the nonwoven material comprises a carded or a spunbound nonwoven material.

6. The stretch laminate according to claim 1, comprising a third layer comprising a nonwoven material, the third layer having a surface that is attached to the first layer on a surface opposite the second layer.

7. The stretch laminate according to claim 6, comprising adhesive disposed between the first layer and the second layer, and disposed between the first layer and the third layer.

8. A method of making a stretch laminate, the method comprising:
    providing an elastomer film,
    the elastomer film having an engineering tensile strength, at an engineering strain rate of about 600/s, of at least one of about greater than about 14 MPa for a plain specimen or about greater than about 7 MPa for a notched specimen;

attaching a nonwoven layer having a basis weight of less than about 25 gsm to the elastomer film to form an assembly; and activating the assembly of the elastomer film and the nonwoven layer, wherein activating the assembly comprises ring rolling the assembly using corrugated interengaging rolls.

9. The method according to claim 8, wherein attaching the nonwoven layer to the elastomer film comprises:
applying adhesive to one of the elastomer film or the nonwoven layer; and
disposing the one of the elastomer film or the nonwoven layer on the other of the elastomer film or the nonwoven layer.

10. The method according to claim 8, comprising:
providing another nonwoven layer; and
attaching the another nonwoven layer to the elastomer film to form the assembly.

11. The method according to claim 10, wherein attaching the another nonwoven layer to the elastomer film comprises:
applying adhesive to one of the elastomer film or the another nonwoven layer; and
disposing the one of the elastomer film or the another nonwoven layer on the other of the elastomer film or the another nonwoven layer.

12. An absorbent article having a waist region and a crotch region, the article comprising:
a backsheet having a longitudinal axis;
a topsheet attached to the backsheet and having a body-facing surface;
an absorbent core disposed between the backsheet and the topsheet; and
a stretch laminate defining at least one region of the absorbent article, the stretch laminate comprising:
a first layer comprising an elastomer film, the first layer having a surface; and
a second layer comprising a nonwoven material, the second layer having a basis weight of less than about 25 gsm and a surface that is attached to the surface of the first layer,
the elastomer film having a strength of an engineering tensile strength, at an engineering strain rate of about 600/s, of at least one of about greater than about 14 MPa for a plain specimen or about greater than about 7 MPa for a notched specimen, wherein an assembly comprising the first layer attached to the second layer is activated, wherein activating the assembly comprises ring rolling the assembly using corrugated interengaging rolls.

13. The absorbent article according to claim 12, wherein the elastomer film has an engineering tensile strength, at an engineering strain rate of about 600/s, of greater than about 20 MPa for a plain specimen.

14. The absorbent article according to claim 12, wherein the elastomer film has an engineering tensile strength, at an engineering strain rate of about 600/s, of greater than about 15 MPa for a notched specimen.

15. The absorbent article according to claim 12, wherein the elastomer film has an engineering tensile strength, at an engineering strain rate of about 600/s, of greater than about 20 MPa for a plain specimen and of greater than about 15 MPa for a notched specimen.

16. The absorbent article according to claim 12, wherein the nonwoven material comprises a carded or a spunbound nonwoven material.

17. The absorbent article according to claim 12, wherein the stretch laminate comprises a third layer comprising a nonwoven material, the third layer having a surface that is attached to the first layer on a surface opposite the second layer.

18. The absorbent article according to claim 17, wherein the stretch laminate comprises adhesive disposed between the first layer and the second layer, and disposed between the first layer and the third layer.

19. The absorbent article according to claim 12, wherein the at least one region comprises a waist region, and the stretch laminate is attached to the backsheet.

20. The absorbent article according to claim 12, wherein the at least one region comprises a side flap, and the stretch laminate is attached to the backsheet.

21. The absorbent article according to claim 20, wherein a fastener is attached to the side flap.

* * * * *